(12) United States Patent
Mohl et al.

(10) Patent No.: US 11,969,587 B2
(45) Date of Patent: Apr. 30, 2024

(54) STENT PUMP

(71) Applicant: Werner Mohl, Altenmarkt/Thennenberg (AT)

(72) Inventors: Werner Mohl, Altenmarkt/Thennenberg (AT); Gerd Siekmeyer, Kiel (DE)

(73) Assignee: Werner Mohl, Altenmarkt/Thennenberg (AT)

( * ) Notice: Subject to any disclaimer, the term of this patent is extended or adjusted under 35 U.S.C. 154(b) by 686 days.

(21) Appl. No.: 17/253,020

(22) PCT Filed: Jun. 18, 2019

(86) PCT No.: PCT/IB2019/055100
§ 371 (c)(1),
(2) Date: Dec. 16, 2020

(87) PCT Pub. No.: WO2019/244031
PCT Pub. Date: Dec. 26, 2019

(65) Prior Publication Data
US 2021/0121679 A1    Apr. 29, 2021

(30) Foreign Application Priority Data

Jun. 18, 2018 (AT) .................................. A 177/2018
Dec. 3, 2018 (AT) .................................. A 364/2018

(51) Int. Cl.
*A61M 60/419* (2021.01)
*A61M 60/135* (2021.01)
(Continued)

(52) U.S. Cl.
CPC ........ *A61M 60/812* (2021.01); *A61M 60/135* (2021.01); *A61M 60/17* (2021.01);
(Continued)

(58) Field of Classification Search
CPC ...... A61M 2205/0266; A61M 2206/20; A61M 60/135; A61M 60/139; A61M 60/165;
(Continued)

(56) References Cited

U.S. PATENT DOCUMENTS 8,690,749 B1    4/2014 Nunez
2014/0275726 A1    9/2014 Zeng
(Continued)

FOREIGN PATENT DOCUMENTS

WO    2009/099644 A1    8/2009
WO    2013/167432 A1    11/2013
WO    2015/160980 A1    10/2015

OTHER PUBLICATIONS

International Search Report dated Oct. 29, 2019 issued in corresponding International Patent Application No. PCT/IB2019/055100 (4 pgs.).
(Continued)

*Primary Examiner* — George Manuel
(74) *Attorney, Agent, or Firm* — Pillsbury Winthrop Shaw Pittman, LLP

(57) ABSTRACT

The invention relates to a stent pump for intravascular, intraventricular or intraatrial placement inside the human heart comprising: —a preferably tubular housing having an inlet and an outlet, —an impeller, and —a stream former, wherein the impeller and optionally the stream former are arranged within the housing, characterized in that the stream former is arranged downstream of the impeller, and the housing, the stream former and/or the impeller are deployable from a first position, in which the housing, the stream former and/or the impeller are folded for being arranged within a delivery device, into a second, expanded position, in which the housing, the stream former and/or the impeller are deployed.

16 Claims, 14 Drawing Sheets

(51) Int. Cl.
*A61M 60/17* (2021.01)
*A61M 60/216* (2021.01)
*A61M 60/808* (2021.01)
*A61M 60/812* (2021.01)
*A61M 60/861* (2021.01)

(52) U.S. Cl.
CPC ........ *A61M 60/216* (2021.01); *A61M 60/419* (2021.01); *A61M 60/808* (2021.01); *A61M 60/861* (2021.01); *A61M 2205/0266* (2013.01); *A61M 2206/20* (2013.01)

(58) Field of Classification Search
CPC .. A61M 60/17; A61M 60/174; A61M 60/216; A61M 60/232; A61M 60/405; A61M 60/414; A61M 60/419; A61M 60/808; A61M 60/812; A61M 60/814; A61M 60/861
See application file for complete search history.

(56) References Cited

U.S. PATENT DOCUMENTS

2015/0051435 A1  2/2015  Siess et al.
2015/0367050 A1* 12/2015  Bulent ................ A61M 60/569
                                                    600/16

OTHER PUBLICATIONS

Written Opinion of the International Searching Authority dated Oct. 29, 2019 issued in corresponding International Patent Application No. PCT/IB2019/055100 (8 pgs.).

International Preliminary Report on Patentability dated Aug. 20, 2020 issued in corresponding International Patent Application No. PCT/IB2019/055100 (16 pgs.).

* cited by examiner

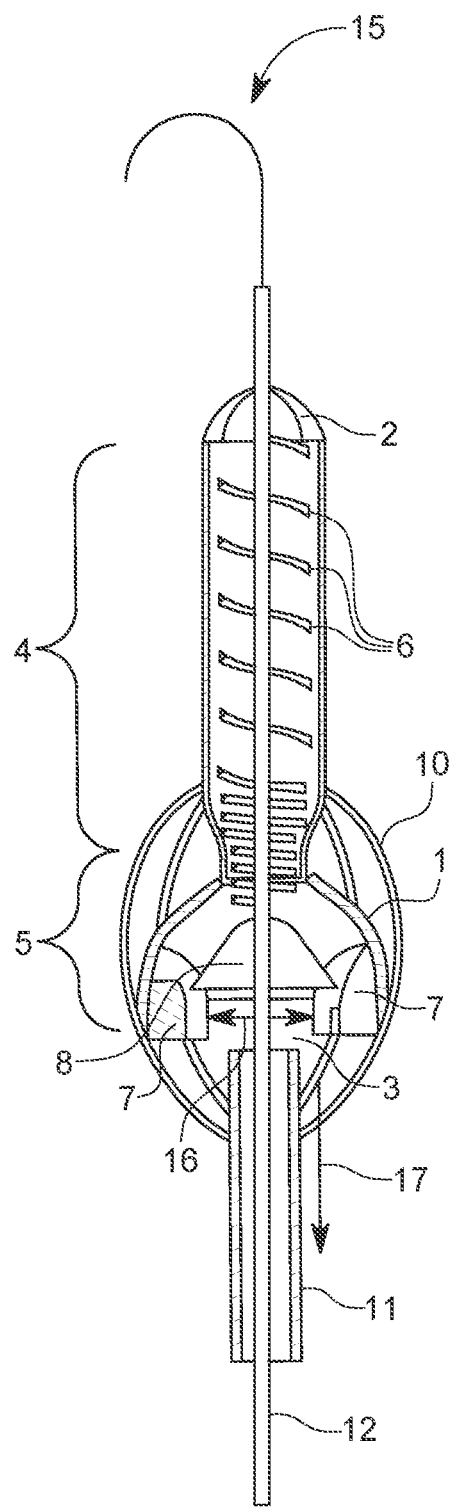
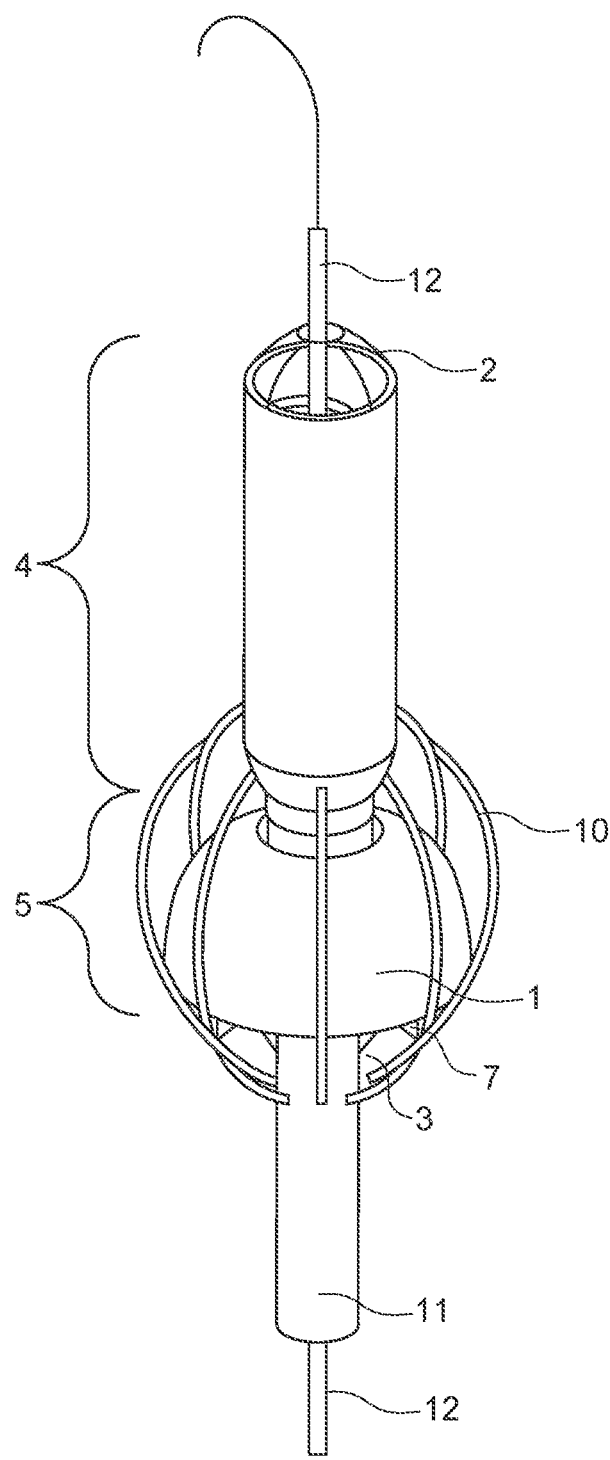
FIG. 2a
FIG. 2b

STENT PUMP

CROSS-REFERENCE TO RELATED APPLICATIONS

This application is a national stage entry of PCT/IB2019/055100, filed Jun. 18, 2019, which claims priority to Austrian Application No. A0177/2018, filed Jun. 18, 2018, and Austrian Application No. A0364/2018, filed Dec. 3, 2018, the entire contents of all of which are herein incorporated by reference in their entireties.

The invention refers to a stent pump for intraatrial, intraventricular or intravascular, preferably intraaortic placement inside the human heart comprising a preferably tubular housing having an inlet and an outlet, an impeller, and a stream former, wherein the impeller and optionally the stream former are arranged within the housing.

Left ventricular contractility normally accelerates blood within the left ventricle and ejects as an average 70% of the blood volume contained in the left ventricle into the circulatory system. In case of severe heart failure this mechanism is insufficient and the majority of the blood volume remains within the ventricle, thus producing inadequate cardiac output.

Several systems are known to correct cardiac failure either temporary or permanently by-passing the left ventricle and continuously ejecting the blood from the left ventricle via an artificial conduit directly into the great thoracic arteries. Such systems operate as left ventricular assist devices (LVAD) in order to help the heart's weakened left ventricle to pump blood throughout the body.

Furthermore, several minimal invasive forms of cardiac assist devices have been developed. WO 2009/099644 A1 discloses a ventricular assist device for intraventricular placement inside a human heart, which comprises a pump that is implanted within the left ventricle with the outflow cannula projecting through the aortic valve and terminating short of the aortic arch.

Many different pump systems for assisting cardiac output are known, for example impeller pumps, gear pumps, piston pumps, vacuum pumps and the like. A typical pump uses an impeller or a set of blades, which spins to push a flow of fluid in one direction.

One major drawback of said known systems is that they require major surgical intervention to be implanted. Secondly hemolysis, i.e. the lysis of red blood cells and the release of their cytoplasm into the surrounding fluid, is favored, because of the undamped ejection of the blood out of the ventricle and its impact on the vessel wall caused by conventional pump systems.

Therefore, it is an object of the instant invention to provide an improved stent pump for intravascular, preferably intraaortic, intraatrial or intraventricular placement (i.e. inside a human heart). In particular, it is an object of the invention to optimize blood flow while simultaneously avoiding damage of red blood cells. In particular, it is an object of the present invention to provide a stent pump that can be easily deployed to the heart in a transcatheter intervention without a sternotomy.

Furthermore, systemic perfusion is stabilized and augmented. If needed, also complete revascularization can be performed and myocardial blood flow is maintained, whereby all of said conditions can be established without major surgical intervention. Lung perfusion is augmented in case of right atrial placement of the stent pump and intrapulmonary outflow.

In order to achieve said objects the stent pump according to the invention is characterized in that the stream former is arranged downstream of the impeller, and the housing, the stream former and/or the impeller are deployable from a first position, in which the housing, the stream former and/or the impeller are folded for being arranged within a delivery device, into a second, expanded position, in which the housing, the stream former and/or the impeller are deployed.

By the inventive combination of the impeller with the stream former, which is arranged downstream of the impeller, in its deployed, i.e. unfolded state, maximal pumping capacity is achieved while the blood flows due to suction into the housing as well as when the blood leaves the pump, whereby turbulent flow and unnatural, abrupt changes in velocity within the pump are avoided. For being arranged at a desired position within a body vessel, the inventive pump is first folded for being received in a delivery device, such as a catheter, and the delivery device is then moved to the target position, where the pump is caused to leave the delivery device and to unfold so as to expand in the radial direction. To bring the pump into its desired position a steerable guiding wire is used, with which the pump is deployed afterwards, whereby the foldable/expandable parts of the pump are expanded. In particular, the impeller is caused to expand in the radial direction so as to increase its pumping capacity. In particular, an increase pumping capacity is provided at a low speed of rotation when compared to prior art intravascular impellers that can be delivered transcatheterally. Preferably, the impeller, in its radially expanded state, has a diameter of 30-75 French, i.e. 10-25 mm, which allows for a lower rotational speed, which in turn avoids blood trauma, while providing for the same hemodynamic performance as known impellers with higher rotational speeds.

In its folded state the inventive stent pump preferably shows a diameter of less or equal to 18 French, i.e. 6 mm in diameter, preferably less or equal to 12 French, i.e. 4 mm. In a preferred embodiment of the invention, the impeller is configured to rotate with 12.500 rpm or less. A rotational speed of, e.g., only 12.000 rpm is sufficient for the pump to convey 4 L/min of blood against a physiologic pressure of 125 mmHg.

In order to achieve less invasiveness the stent pump according to the invention has a diameter as small as possible, which serves for easy deployment. In its deployed state the diameter of the pump is as large as possible, which allows for a low rotational speed in order to avoid damage to blood components, whereby global hemodynamics are generally supported.

Furthermore, the rotational speed may be adapted according to the actual needs of the patient and both continuous or pulsatile flow patterns can be achieved.

To achieve optimal function a pulsatile higher speed of the pump is needed during systole and a pulsatile lower speed during diastole. Sensing of arterial pressure as resistance to flow may be used as driving parameter as well as the volume in the ventricle measured as conductance.

Said measurements may preferably be realized by at least one sensor comprised in the pump, which allows measurement of the volume of fluid per unit of time or determination of measured quantities, which are proportional to the volume. The sensor might be connected to an evaluation circuit in which the ratio of the diastolic volume to the systolic volume per heartbeat or unit of time, especially the output rate and/or the deviation of the volume, which has been delivered by the heart per unit of time from a defined setpoint, for example the setpoint which has been computed from body-specific data for the cardiac output, is evaluated and a signal is generated, whereby the pump might be controlled depending on the generated signal.

The delivery performance of the pump might be increased at a low output rate and at low delivery performance of the heart, and might be reduced at correspondingly higher measured values. The delivery performance of the pump might thus be controlled primarily such that overall an output rate, which corresponds to a healthy heart, is simulated. More preferably, the pump can be arranged such that its delivery performance is controlled as a function of the measured values for the output rate up to achieving an output rate between 65 and 80%.

In addition to the output rate as a measure for the required correction measures and especially as a control signal for the performance of the pump, preferably a setpoint, which has been computed from body-specific data, can be used for the cardiac output as a measured quantity.

On the contrary, continuous action of the pump might be needed in case of total dependency of global hemodynamics from the artificial pump action.

Preferably, the stent pump may be deployable in its axial and/or its radial direction, whereby the radial expansion is necessary to provide enough space for the subsequent longitudinal expansion. Longitudinal expansion in the sense of the present invention is to be understood as the correct arrangement of the individual components of the stent pump after deployment, such as the pushing of the impeller into the housing, which was deployed beforehand.

According to a preferred embodiment of the invention, the impeller is arranged to be displaceable in an axial direction relative to the housing between a first and a second axial position, wherein in its first axial position the impeller is arranged outside the housing, when the impeller and the housing are folded for being arranged within a delivery device, and in its second axial position the impeller is arranged within the housing, when said housing and said impeller are deployed. By arranging the impeller outside of the housing when the pump is delivered by means of a delivery device, such as a catheter, the housing may be folded down to a minimum size so as to minimize the space needed within the delivery device. Once the pump has been positioned at its target site, the housing and the impeller are deployed, i.e. expanded radially, separately such that the impeller may subsequently be displaced axially to be placed inside the housing.

Due to its rotation and geometric shape the impeller attracts the blood flow through the housing and serves for an increase of the blood pressure and the blood flow. The pump is preferably formed as a centrifugal pump that ejects the blood in an essentially radial direction. The blood is transported by the vanes or rotor blades of the impeller, radially ejected and conveyed to the stream former, which subsequently serves for ejecting the blood axially into the vessel, while damping its flow at the same time.

The inlet and the outlet of the housing or at least the part of the housing, in which the impeller and/or the stream former are arranged, may be arranged within the ascending aorta or within the left ventricle or between the ascending aorta and the left ventricle or within the left atrium or between the left atrium and the ascending aorta or within the right atrium or between the right atrium and the arteria pulmonalis.

In order to enable the pump components to return to their original shape, to resist the varying pressure prevailing in the heart and hence acting on said components, and to serve for a long living and functioning stent pump, the housing and/or the stream former and/or the impeller are preferably made of a shape-memory alloy, such as e.g. nitinol.

Preferably, the pump further comprises a preferably flexible drive for driving a mandrel arranged within the housing and fixed to the impeller. Preferably, the drive is an electric, hydraulic or pneumatic motor.

The mandrel may preferably be arranged in a semipermeable tube with a hygroscopic inner surface and a hyperosmolar outer surface, such as e.g. a polymer hose, such as a teflon, FEP or PEEK hose. Said surface design leads to removal of the salty components from the blood stream and their transport to the outer surface of the tube. Furthermore, watery components from outside the tube enter the tube and are conveyed via the rotational flow inside the pump housing. Hence coagulation of blood inside the pump and heating of the individual components is prevented.

Furthermore, the pump may preferably comprise a magnetic coupling, which couples the mandrel to the drive. The magnetic coupling provides a non-contact and wearless transmission of the rotary motion of the drive to the impeller. Further, the magnetic coupling facilitates the removal of the drive and the mounting of a new drive if needed.

Preferably, the magnetic coupling and/or the drive are arranged outside the vessel or the ventricle, preferably outside the human body. Said arrangement also favors easy deployment to the heart without a sternotomy, because the bulky components, as e.g. the drive must not be implanted in the heart, but may be kept outside in the pericardial sack, outside the vascular system or the human body, respectively.

More preferably, the drive and the stream former may be built as one piece and arranged within the housing of the pump.

Preferably, the housing has a wall that is impermeable to blood, which ensures for an unimpaired and precisely directed transport of the pumped blood.

Alternatively, the wall of the housing may partly be permeable or completely permeable to blood.

More preferably, the wall of the housing is configured as a flexible hose or as a cage made of wire or cut from a stent tube and carrying a flexible jacket, such as, e.g., a cage or a wire helix made from a laminated wire, the lamination preferably being made of PET, silicone or PTFE.

Preferably, the housing may be configured as double-walled flexible hose, wherein a wire helix is arranged between the two walls of the double-walled hose.

In order to fix the stent pump in the ventricle or the vessel, the housing preferably comprises fixing means for fixing the housing in a vessel, such as a fixing cage.

The fixing means may preferably comprise an anchor element, which is e.g. fixed to the wall of the heart near the apex in order to hold the stent pump in its position.

Alternatively, the fixing means may preferably comprise a radially expandable and blood permeable element, such as, e.g., a radially expandable cage, that surrounds the housing, whereby such expandable element provides a radial distance between the vessel wall and the housing of the pump for allowing blood to flow through an annular cross section between the vessel wall and the housing of the pump. With the aid of said fixing means the housing—when expanded radially or when alternatively being equipped with spacers—has a similar function as a stent, whereby the expanded element or the spacers rest against the wall of the vessel.

Since the blood should be allowed to by-pass the housing of the pump, which is preferably impermeable to blood, the fixing means may preferably be built permeably, which can e.g. be achieved via using a permeable net structure or the like.

When spacers are used as fixing means, they may be arranged around the housing, whereby a certain distance is left between the individual spacer elements, which in turn causes permeability in the region where the spacers are arranged.

In order to minimize the amount of separate parts and to provide a compact construction of the pump, the radially expandable element is not formed by a separate element, such as a separate cage surrounding the housing, but may preferably be formed by a distal section of the housing, which in its expanded state preferably widens in the flow direction.

Preferably, the stream former may be arranged in said radially expandable element. In particular, the stream former may be arranged to impart an axial flow direction not only to the blood being pumped by the impeller, but also to the blood that flows through an annular cross section between the vessel wall and the housing of the pump.

When the pump is deployed from its first position, in which the housing, the stream former and/or the impeller are folded for being arranged within a delivery device, into its second position, in which the housing, the stream former and/or the impeller are deployed, the radially expandable element is widened in its radial direction until it rests against the vessel wall. Thereby sufficient space for the deployed impeller and optionally the deployed stream former to be arranged within the housing is offered and the vessel is forced to stay open.

According to the invention the impeller, which is—in the deployed state of the pump—arranged upstream of the stream former, has to be arranged within the housing, preferably near its outlet. The stream former may also be arranged within the housing, but may also be arranged outside of the housing, in both of said configurations preferably also near the outlet of the housing.

When the stent pump is arranged within the ascending aorta, the upstream end of the pump, i.e. the inlet section of the housing, is arranged in the left ventricle and the downstream end of the pump, i.e. the part in the region of the outlet of the housing, is arranged shortly upstream or shortly downstream the aortic valve. In said configuration the deployed housing shows a tulip-shape, whereby the outlet region of the housing is widened and the impeller and optionally the stream former are arranged within said widened part.

When the stent pump is arranged within the left ventricle, the arrangement of the inlet and the outlet of the pump correspond to the above mentioned arrangement, i.e. the inlet section is arranged in the ventricle and the outlet is situated near the aortic valve, but the deployed housing has to have a different shape. The "tulip" of the tulip-shape part has to be elongated, because in order to achieve sufficient acceleration and transport of the blood, the impeller and the stream former cannot be arranged too far apart from the inlet of the housing. Since in said configuration the upstream end of the tulip-shape part of the housing is likely to be arranged in the ventricle, the following part has to extend through the aortic valve and to end in the ascending aorta and hence to be elongated if compared to the embodiment where the pump is placed in the ascending aorta. The impeller and the stream former are again arranged within the "tulip", preferably near the upstream end of the tulip-shape part of the housing.

When the stent pump is arranged within the left atrium the upstream end of the pump, i.e. the inlet section of the housing is arranged in the left atrium near the septum of the heart, whereby shortly downstream the inlet section the impeller and the stream former are arranged, and the downstream end of the pump, i.e. the outlet section of the housing comprises a long cannula being arranged downstream of the stream former and mouthing in the aortic valve. In said configuration the deployed housing may also show a tulip-shape, whereby the inlet region of the housing is widened and the impeller and optionally the stream former are arranged downstream said widened part. In other words, the inlet section is funnel shaped, funneling towards the upstream part of the pump. Alternatively, funnel shaped means, which are arranged upstream of the impeller in the inlet section of the pump and which direct the incoming blood flow towards the impeller, are provided. The funnel shaped inlet section or funnel shaped means may also be expandable.

Furthermore, the drive of the pump may be arranged near the impeller, preferably on the left side of the septum, and the tulip shaped inlet part of the housing, which may be equipped with the stream former, may be fixed to the drive, whereby a magnetic coupling and a short central wire connects to the impeller. The outlet part of the housing may comprise an outlet cannula.

The stent pump may be deployed and implanted with a plurality of wires, such as a guide wire for positioning the pump, a rotational wire, which is coupled to the pump and the drive, a pushing/pulling wire used to unfold the device and a stabilizing wire for holding the pump in its desired position.

The pushing/pulling wire moves the impeller from the first position (folded position), in which the impeller is arranged downstream of the stream former, into the second position (unfolded, expanded position), in which the impeller is arranged upstream of the stream former. Furthermore the pulling/pushing wire allows the expansion of the housing, the impeller, the fins of the stream former and the fixing means.

The impeller pumps the blood that is being sucked out of the ventricle into the housing via the upstream part of the housing, which may serve as a suction hose.

Said upstream part of the housing may preferably be perforated and hence be permeable to blood, which is especially advantageous when the pump is implanted in the left ventricle of the human heart. The rotation of the impeller, which is located inside the housing, leads to attraction of the blood out of the ventricle through the perforated part of the housing to the inside of the pump.

In said configuration the part of the housing, which follows said upstream part in the downstream direction, i.e. the "tulip-shape" part, preferably comprises an impermeable wall.

When the pump is implanted in the aortic arch the "tulip-shape" part may comprise an impermeable or permeable wall.

The inflow and/or the outflow part of the housing may preferably be perforated and hence be permeable to blood in order to enable attraction of the blood surrounding the housing to the inside of the housing, when the impeller of the stent pump is rotated (water jet principle).

When being arranged within the ventricle the pump provides for a pulsatile, i.e. intermittent, flow acceleration of the blood, preferably during systole. Preferably, the pulsatile flow acceleration is synchronized with the heartbeat.

In order to provide pulsatile flow acceleration during systole, the pump may preferably be equipped with a control unit connected with the drive of the pump, said control unit comprising a first sensor for sensing a heartbeat of the heart and configured to control the pump to be driven in a pulsatile manner in synchronization with the heartbeats as well as resistance to rotation according to the back-pressure in the arterial system.

Alternatively, when the pump is arranged in the ascending aorta the pump provides a continuous, non-pulsatile flow acceleration of the blood.

Preferably, the housing is divided in at least two axial sections and comprises an inlet section and an impeller section, the inlet section being arranged upstream of the impeller section.

In order to favor a smooth entry of the blood stream into the impeller it may be desired to impart a spin on the blood flow before the blood flow reaches the impeller. Hence, the housing preferably comprises, in particular in its inlet section, means for imparting a rotational flow component to the blood, such as guiding elements or vanes protruding inwardly from the wall of the housing. The rotational flow component results in a helical flow with the axis of the helix extending in the axial direction of the pump.

Normally blood is accelerated in a laminar flow pattern, although disease may induce turbulent flow.

State of the art support pumps induce suction of the blood out of the left ventricle, whereby the blood flow reaches the impellers without any entrainment, which in turn may cause blood trauma.

In order to achieve a rotational flow pattern and to accelerate the blood before entering the impeller space, the aforementioned means for imparting a rotational flow component to the blood initiate rotational flow of the blood.

Furthermore, the inlet section preferably comprises a tapering cross section at the orifice to the impeller section of the housing, i.e. narrows where the inlet section opens out into the part of the housing where the impeller is arranged when the pump is deployed, whereby a suction effect and hence acceleration of the blood at the tapering cross section is induced.

Preferably, the outlet section comprises preformed flexures to correspond to the anatomy of the left ventricle, which may be built from a shape-memory material, such as e.g. Nitinol.

More preferably, said means are configured such that the blood stream receives a counter-clockwise spin and hence reaches the impeller with said counter-clockwise spin. The impeller preferably also shows a counter-clockwise rotation. By said synchronization hemolysis is prohibited and heating of the blood is avoided.

Alternatively, said means are configured such that the blood stream receives a clockwise spin and the impeller preferably also shows a clockwise rotation, which also results in the desired avoidance of blood trauma and heat generation.

Preferably, the stream former is laminated with e.g. a heparin-coating, which prohibits coagulation and hence blood clotting on the stream former.

Preferably, the impeller comprises a conical body that carries vanes. More preferably, the vanes of the impeller have a hyperboloid shape. Said configuration serves for effective transport and the desired radial ejection of the blood stream before it reaches the stream former.

The space in between the impeller and the housing is arranged such that maximal efficiency and less blood trauma is allowed, i.e. the space has to be chosen neither too narrow, nor too broad, whereas the exact space in between has to be optimized according to fluid dynamics of the impeller and the housing.

The impeller may preferably be equipped with 5 vanes, which exhibit in its deployed state a length of 6-10 mm, preferably 8 mm. The vanes may be fixed in/on a cylindrical tube, which is preferably 2.5 mm in diameter and 10 mm in height, whereby the rotational axis of the impeller is situated along the axis of said tube.

In order to serve for easy deployment into the ventricle or the vessel, the vanes of the impeller are preferably made of preferably foldable wires and/or sheets. Thereby a space-saving embodiment of the individual components is allowed.

The folding of the impeller or deployment, i.e. defolding, of the impeller may preferably be achieved as follows.

Basically the folding may be realized by the furling of thin, flexible and self-expanding Nitinol sheet structures (<100 microns). Firstly, all elements of the impeller are arranged in a vertical direction, from which deployment or crimping is possible.

In order to fold or to deploy the impeller correctly, i.e. to keep it in the vertical plane, or to defold it into the horizontal plane, whereby the impeller reveals its conical shape, a springy wire element may be used which absorbs or releases tensile/compression and torsion forces during the folding deformations. Said flexible wire element thus moves one side of the structured sheets, which form the conical structure of the impeller, up or down, thereby creating a folding mechanism.

The impeller preferably comprises two elements that require a specific geometric shape, namely its fins and the elements forming its conical structure. Preferably, the conical structure has a two-dimensional geometric (hyperbolic) contour, which can only be realized in sheets and foils by structuring, which allows for a multi-dimensional elastic deformation. Said structuring may e.g. be achieved via differentiating the conical structure into smaller segments/structures. The thus formed conical structure of the impeller may then either serve itself as a hyperbolic cone or may built a hyperbolic cone in conjunction e.g. with flexible materials, similar to "auxetic material structures". Thus, elastic multi-dimensional shapes can be produced, which may also serve as supports in connection with e.g. highly flexible polymeric sheet material (e.g. porous Teflon), which enables the open structures to close again.

The fins are arranged by the use of structuring, which aids to create a multi-dimensional transition zone on the axial section of the conical structure, i.e. the section where the drive shaft may be arranged. Thereby, flow-optimized and shaped sheets can again be defolded correspondingly.

Furthermore, a flexible wire structure may be arranged starting on the upstream section of the impeller and ending at the downstream section of the impeller below its fins, which serves as a support element for each individual wing impeller segment as well as can be used to deploy/fold the individual segments by pushing or pulling them, respectively.

Preferably, the stream former comprises substantially parallel fins extending in an axial direction. Preferably, said fins are arranged on the inner surface of the housing. As already mentioned above the blood leaves the impeller in its radial direction. By the substantially parallel oriented fins extending in an axial direction of the stream former, the bloodstream is redirected, i.e. the blood flows in a mostly axial direction when leaving the pump, which provides for a laminar flow. Via said redirecting effect, the desired ejection direction and the desired damping of the blood flow is achieved.

Preferably, the stream former comprises an annular cross section, which connects the impeller with the outlet section, thereby directing the blood from its radially outward position after it leaves the impeller to the outlet section. In particular, the diameter of the annular cross section decreases in the flow direction, i.e. towards the outlet section. According to a preferred embodiment, the annular cross section is formed by a radial distance between the housing and a balloon that is arranged in the housing downstream of the impeller. Preferably, the balloon has a curved outer surface that provides the diameter reduction mentioned above. For example, the balloon may have the shape of a hemisphere or of a semi-ellipsoid. The balloon may be arranged on the rotating mandrel that drives the impeller. Alternatively, the balloon may be arranged in a torque proof manner, so that it does not rotate together with the balloon.

The blood shows laminar flow when entering the stent pump, is subsequently brought into rotation and accelerated in the inlet section of the housing and the impeller region and exits the pump with laminar flow, which is due to the redirection of the rotational flow at the fins of the stream former.

More preferably, the housing may also contain a longitudinal helix, which is arranged between the housing and the impeller and which starts at the inlet section of the housing and ends in the upstream region of the fins of the stream former. Hence the ends of the helix continue into the fins of the stream former, which also aids redirection of the rotational flow at the fins of the stream former.

Alternatively, the longitudinal helix starts at the inlet section of the housing and ends at the outlet section of the housing, whereby the helix on the one hand provides for overall stabilization of the pump housing and on the other hand provides for induction of rotation of the blood flow in the inlet section.

To provide initial rotation in the inlet section, the helix preferably forms a helix-shaped structure that protrudes into the flow cross section of the blood. Where no rotation shall be induced, such as in the section of the stream former and the outlet section, the helix is covered at its inner side facing the blood by a smooth layer, such as a hose.

The layer covering of the helix may be made from PET, silicone or PTFE.

Moreover the components of the deployment-mechanism, the housing and the fins may preferably be built of Nitinol. The mandrel and the required bearings may be made of a surgical metal and the remaining components of the device may be made of a polymer.

The device according to the invention may be deployed sequentially, whereby as a first step the housing and the stream former, both in its folded position, are arranged within a delivery device, e.g. a catheter shaft, and inserted into the left atrium, the left ventricle or the aorta of the human heart, where the two components subsequently self-deploy when the catheter shaft is withdrawn. As a second step the impeller and optionally also the funnel shaped means, also in their folded position, are arranged within the delivery device and also inserted into the human heart until they reach the position, where the housing and the stream former were already deployed. The impeller and optionally the funnel shaped means are then also deployed via withdrawing of the catheter shaft and after its deployment the impeller and optionally the funnel shaped means are pushed into the deployed housing and fixed upstream of the stream former.

The stent pump may be implanted through the aorta, through the apex of the heart or an anonymous vein, whereby—in the case of implantation through an anonymous vein—a temporarily lockable fistula is created to intermittently connect the vena cava superior with the aorta, namely until the pump reaches the aorta, in order to allow delivery of the pump to the aorta.

The stent pump may also be implanted from a large central or peripheral vein, preferably the right femoral vein, whereby the heart is accessed via the vena cava superior or the vena cava inferior (so-called "retrograde approach"), whereby in both cases a catheter sleeve containing the individual components of the pump is advanced through the vena cava into the right atrium with the aid of a steerable guiding wire. When the right atrium is reached the septum between the right and the left atrium is punctured in the region of the foramen ovale in order to advance the guiding wire, the catheter as well as the individual components of the pump into the left atrium. After reaching the left atrium, the guiding wire is pushed towards the aortic valve, whereby in order to reach the aortic valve the guiding wire has to be steered such that it turns twice in an angle of 90 degrees. After positioning the guiding wire, the expandable housing of the pump is positioned along the guiding wire, whereupon the impeller and/or the stream former and/or the funnel shaped means are advanced inside the housing in their folded state, defolded via pulling back the guiding wire and hence placed in the desired position inside the left atrium. In said embodiment the drive of the pump may be arranged inside the right atrium or transseptally, i.e. crossing the septum.

The folded pump and the catheter may be positioned together with a special drive outside diameter of 6 mm and a 4:1 planet transmission into the left atrium and the outflow cannula may then be introduced via the mitral valve, the left ventricle and the aortic valve into the central aorta. The stent pump remains in the left atrium. The outflow cannula mouths in the central aorta and transforms the rotational blood flow into a laminar one. Within the left ventricle additional flow may be forced into the housing via the water jet pump principle.

The "retrograde approach" is a more secure approach for entering the human heart if compared to implantation via the apex or the aorta, since by entering the heart via the vena cava embolisms are effectively prevented.

An experienced interventionist may be able to insert the stent pump transseptally in less then 15 minutes and without major surgery. This retrograde access is preferred since no atherosclerotic emboli can be mobilized when the stent pump is deployed, whereby the risk of cerebral stroke is limited.

Preferably, the fins of the stream former are realized as an integral part of the housing.

In the following the present invention will be described by some exemplary embodiments.

FIG. 1a shows a sectional view of the stent pump in its folded state and

FIG. 1b a perspective view of the stent pump in its folded state, both according to a first embodiment of the present invention.

FIG. 2a shows a sectional view of the stent pump in its unfolded, expanded state and FIG. 2b a perspective view of the stent pump in its unfolded, expanded state according to the first embodiment as depicted in FIGS. 1a and 1b.

Figure 4A:
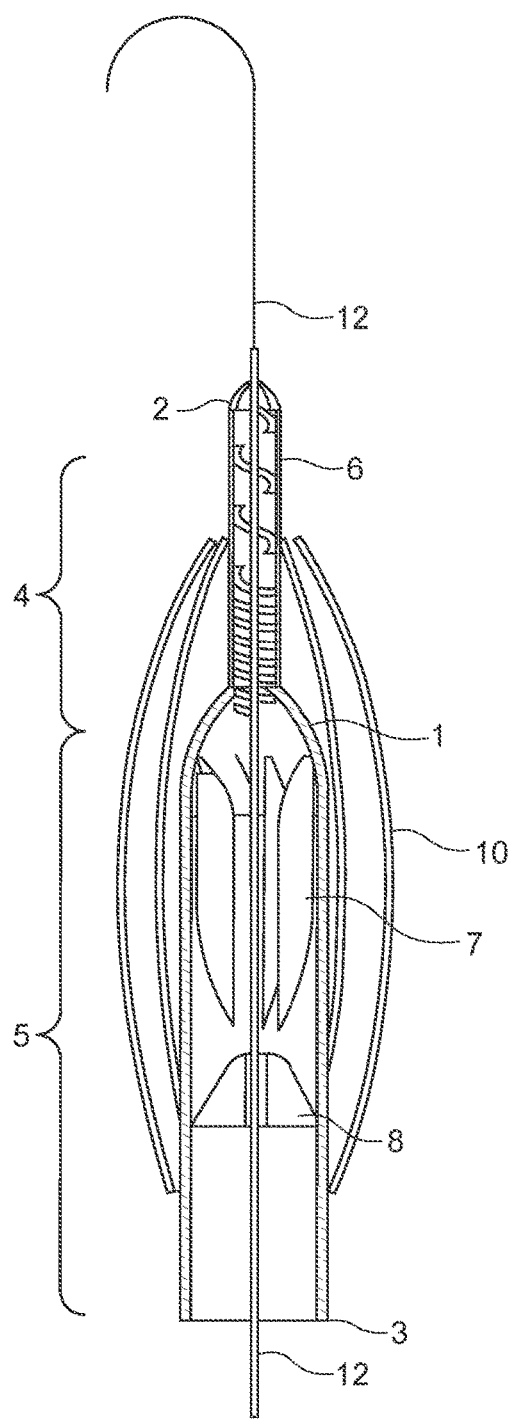
FIG. 4a shows a sectional view of the stent pump in its folded state.
Figure 4B:
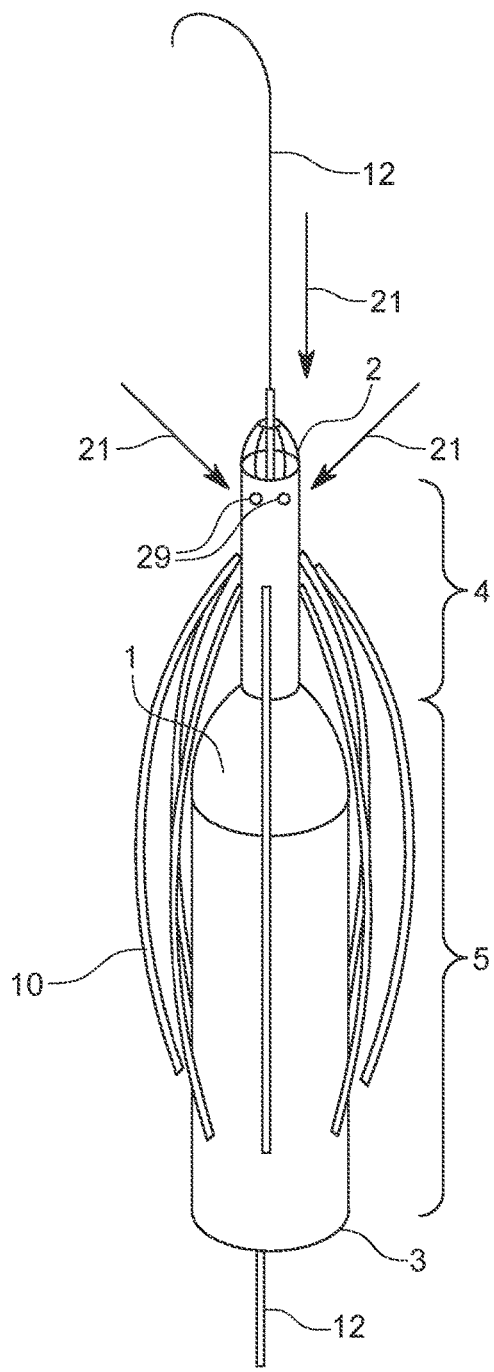

FIG. 4b a perspective view of the stent pump in its folded state, both according to a second embodiment of the present invention.

Figure 5A:
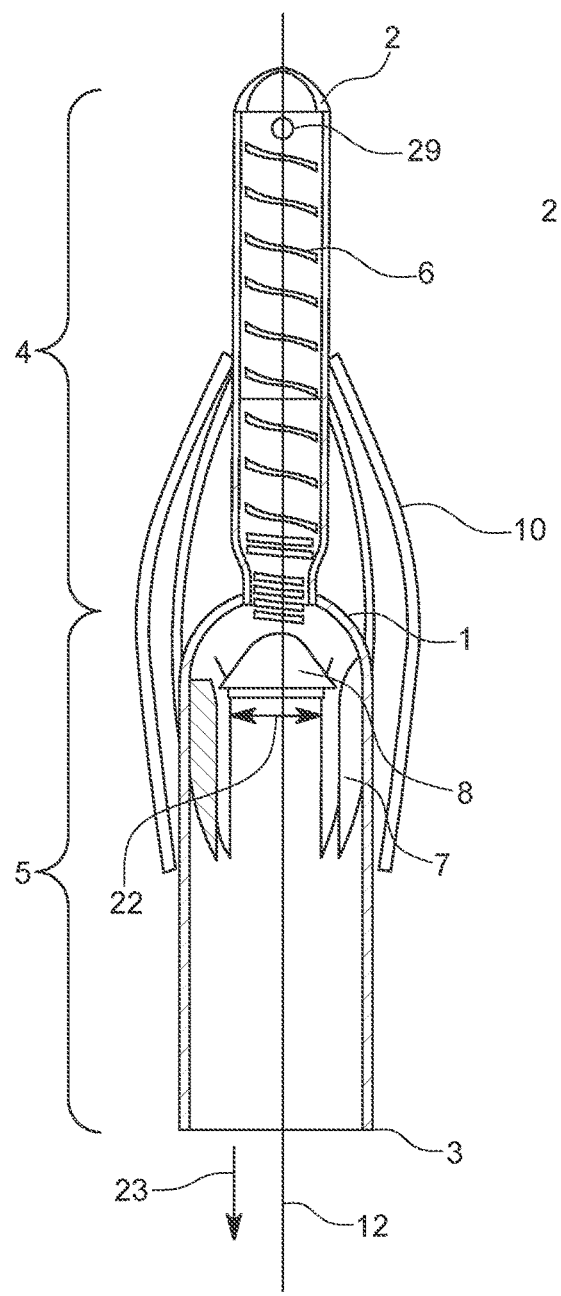
Figure 5B:
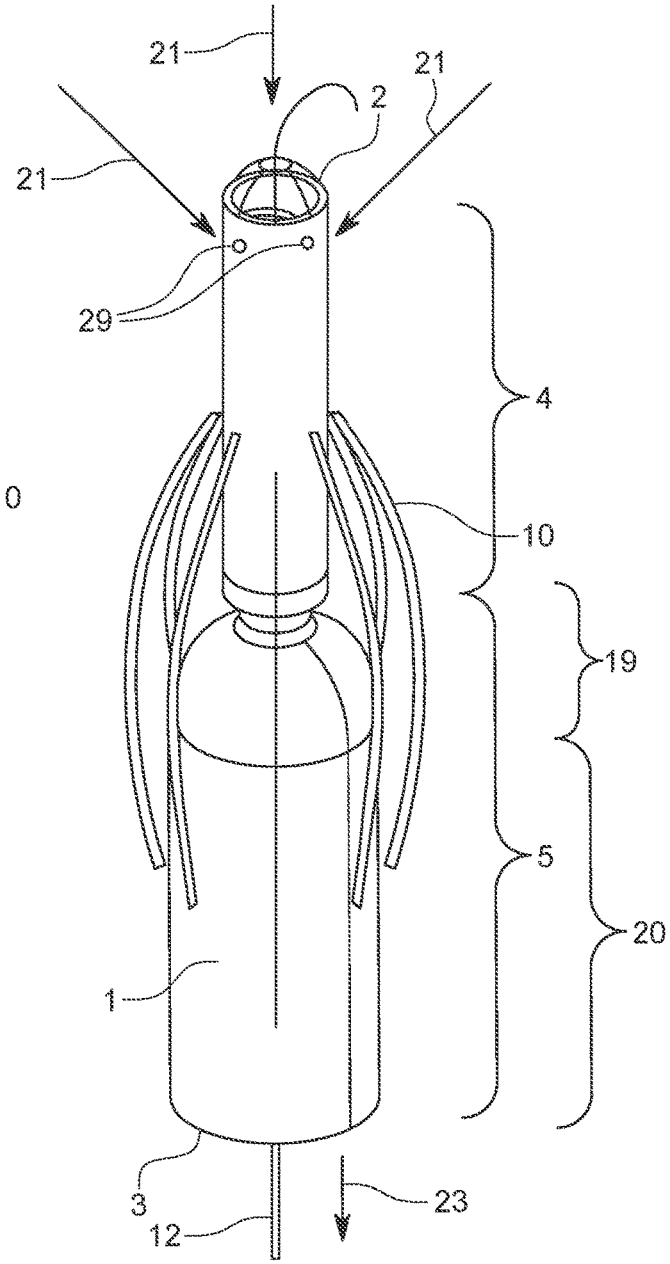

FIG. 5a shows a sectional view of the stent pump in its unfolded, expanded state and FIG. 5a and FIG. 5b a perspective view of the stent pump in its unfolded, expanded state according to the second embodiment as depicted in FIGS. 4a and 4b.

Figure 6:
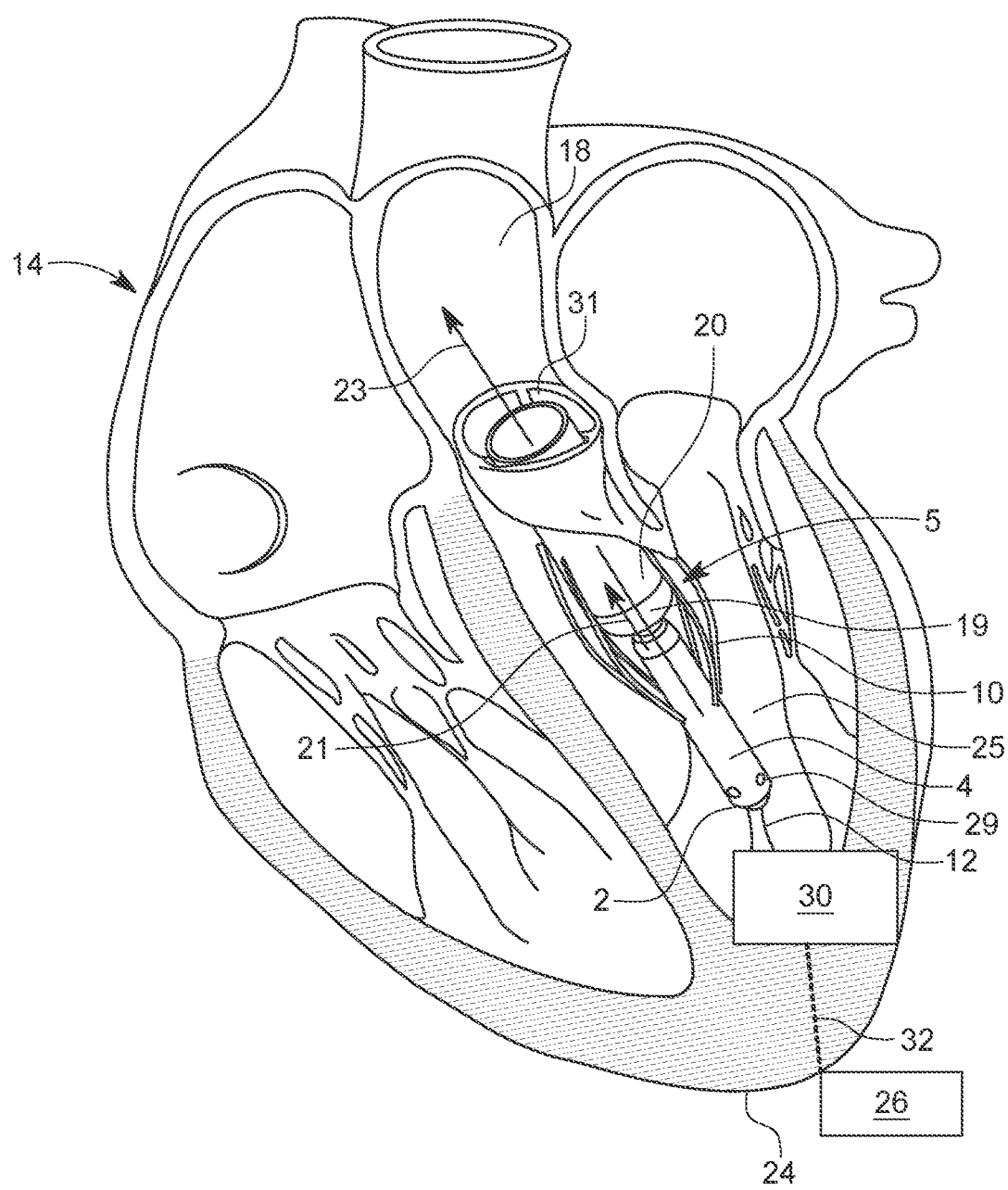

FIG. 6 shows the human heart with the stent pump according to the second embodiment as depicted in FIGS. 4a and 4b and FIGS. 5a and 5b when being implanted in the left ventricle.

Figure 7:
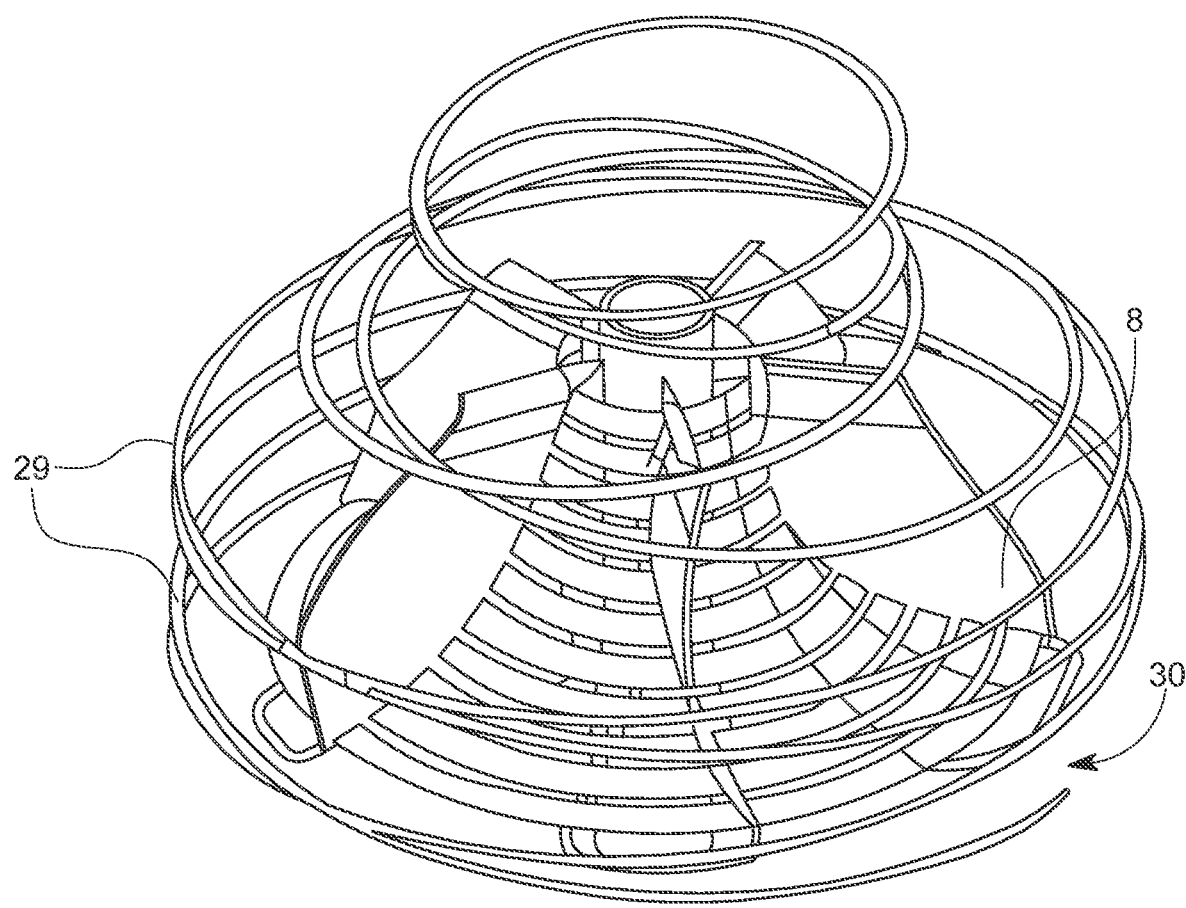

FIG. 7 is a perspective detailed view of the impeller surrounded by a wall of the housing of the pump, which is configured as longitudinal helix according to a third embodiment of the invention.

Figure 8:
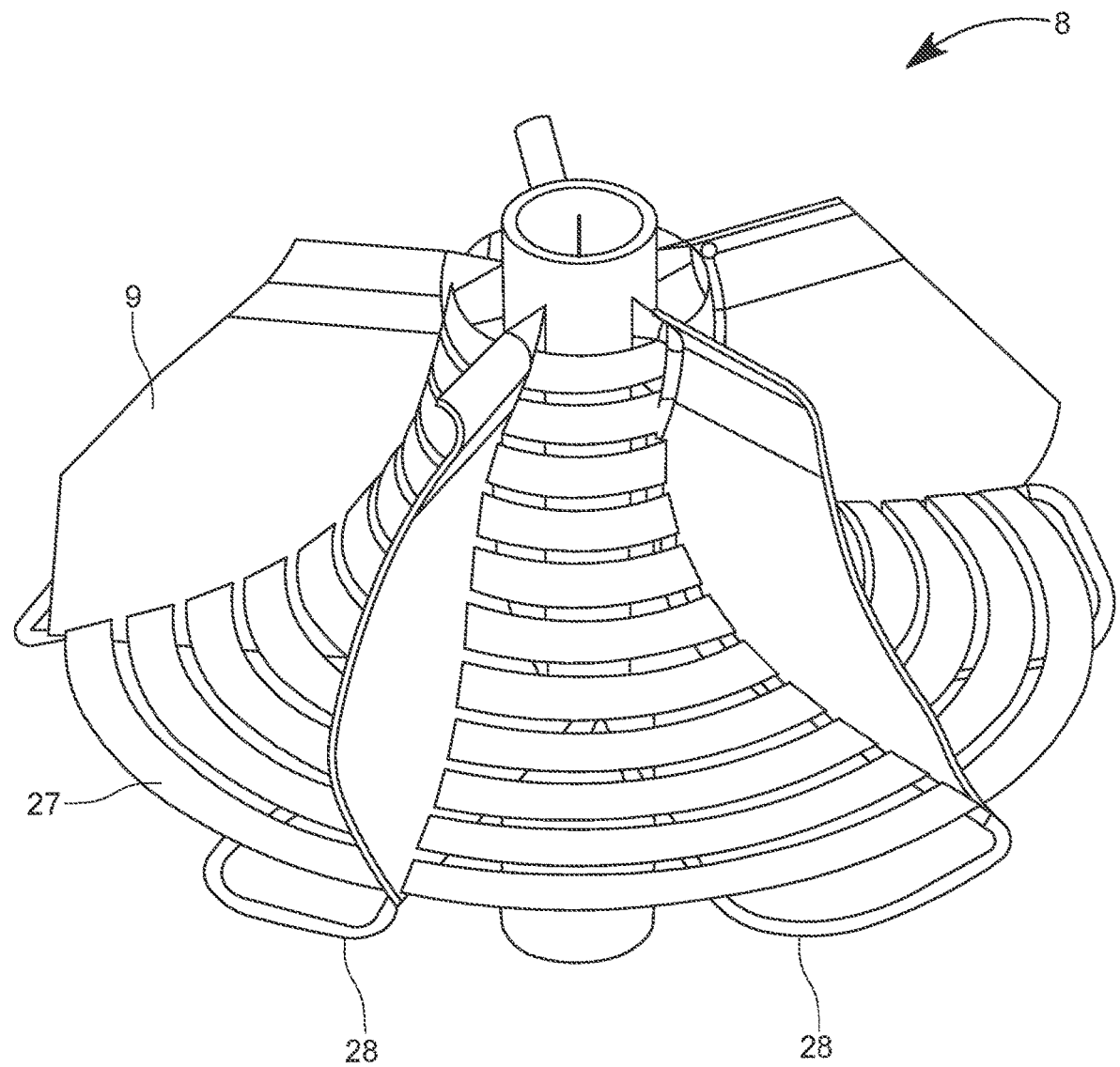

FIG. 8 is a detailed view of the impeller.

Figure 9:
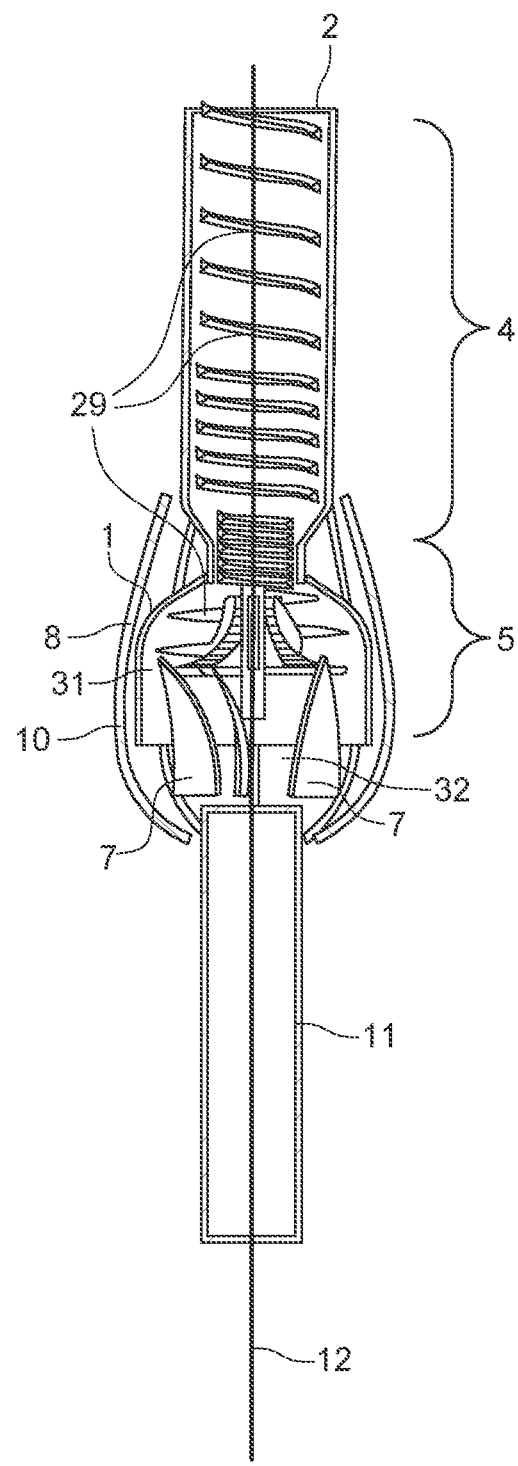

FIG. 9 is a sectional view of the stent pump in its unfolded, expanded state according to the third embodiment of the present invention as depicted in FIG. 7.

Figure 10:
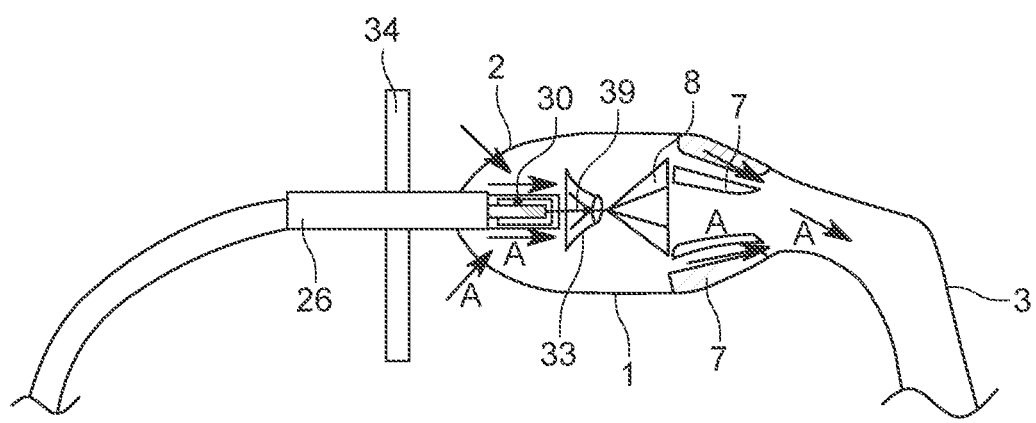

FIG. 10 shows a sectional view of the stent pump according to a fourth embodiment of the invention in its unfolded, expanded state.

Figure 11:
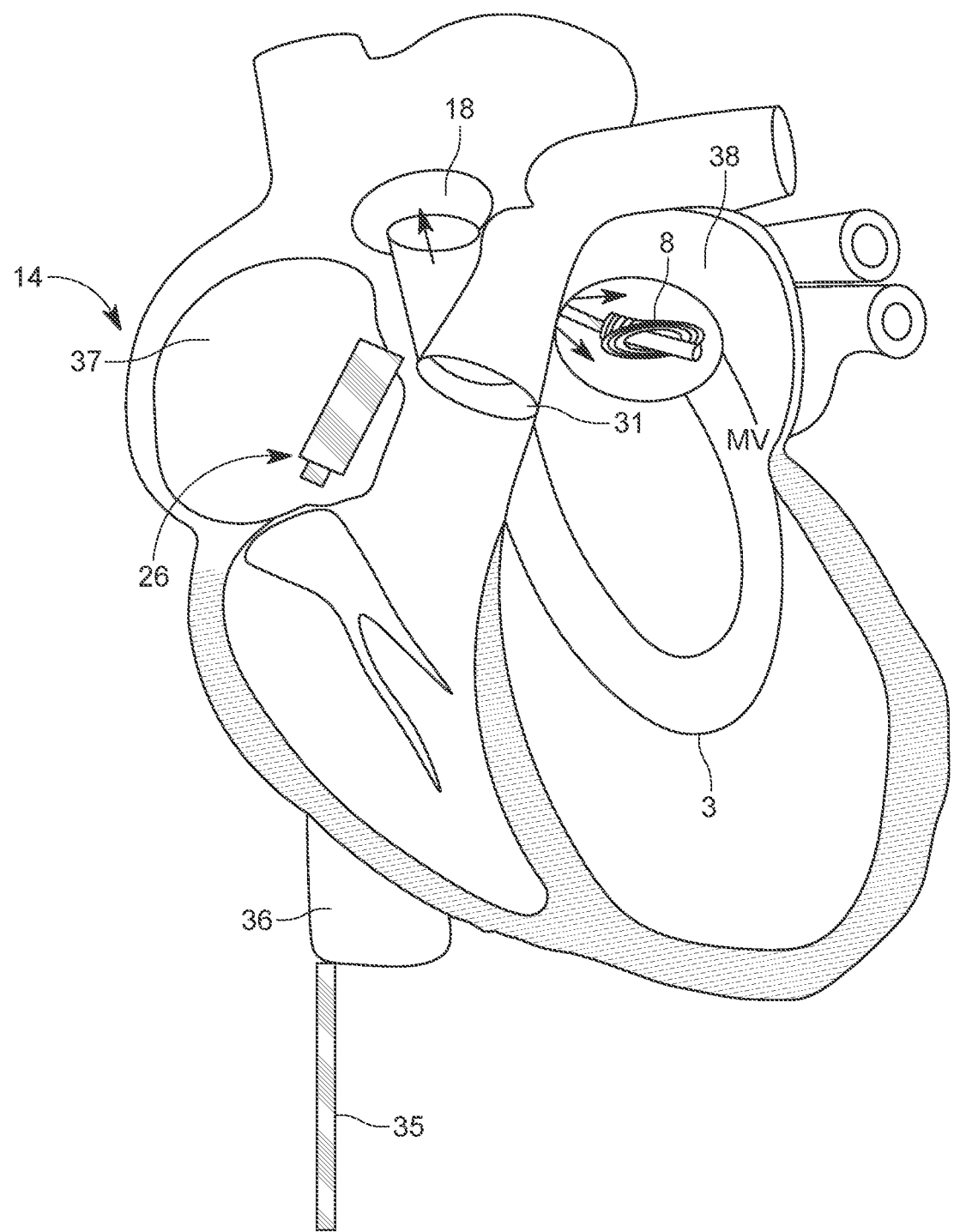
Figure 12:
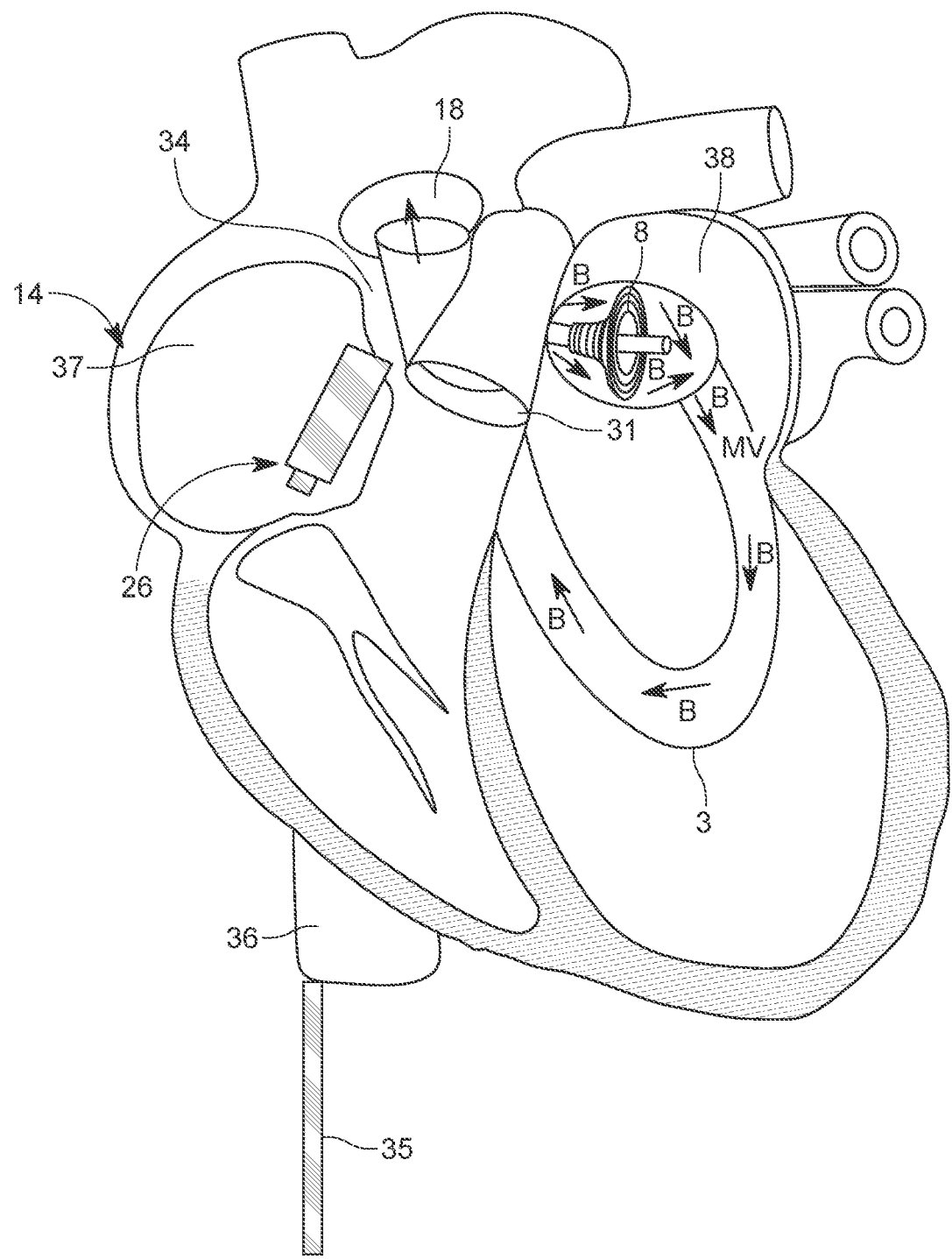
Figure 13:
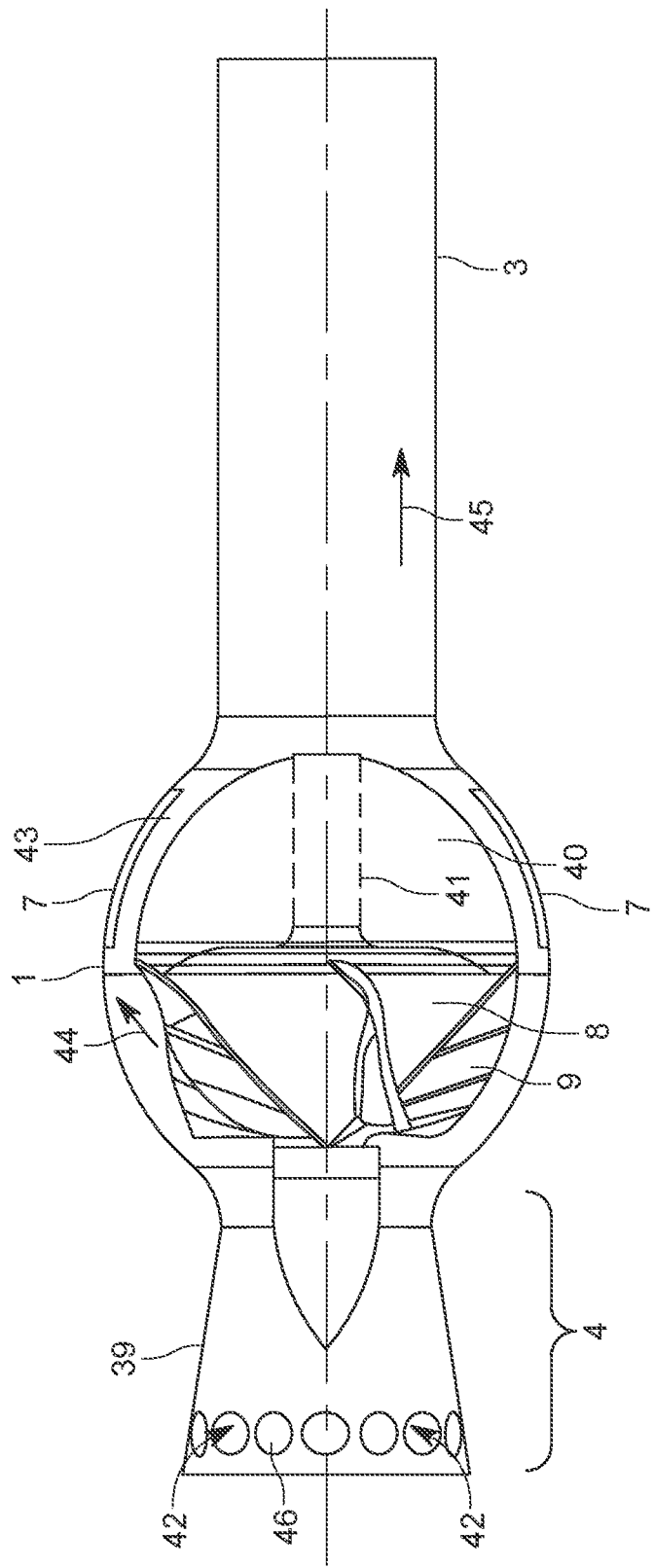
Figure 14:
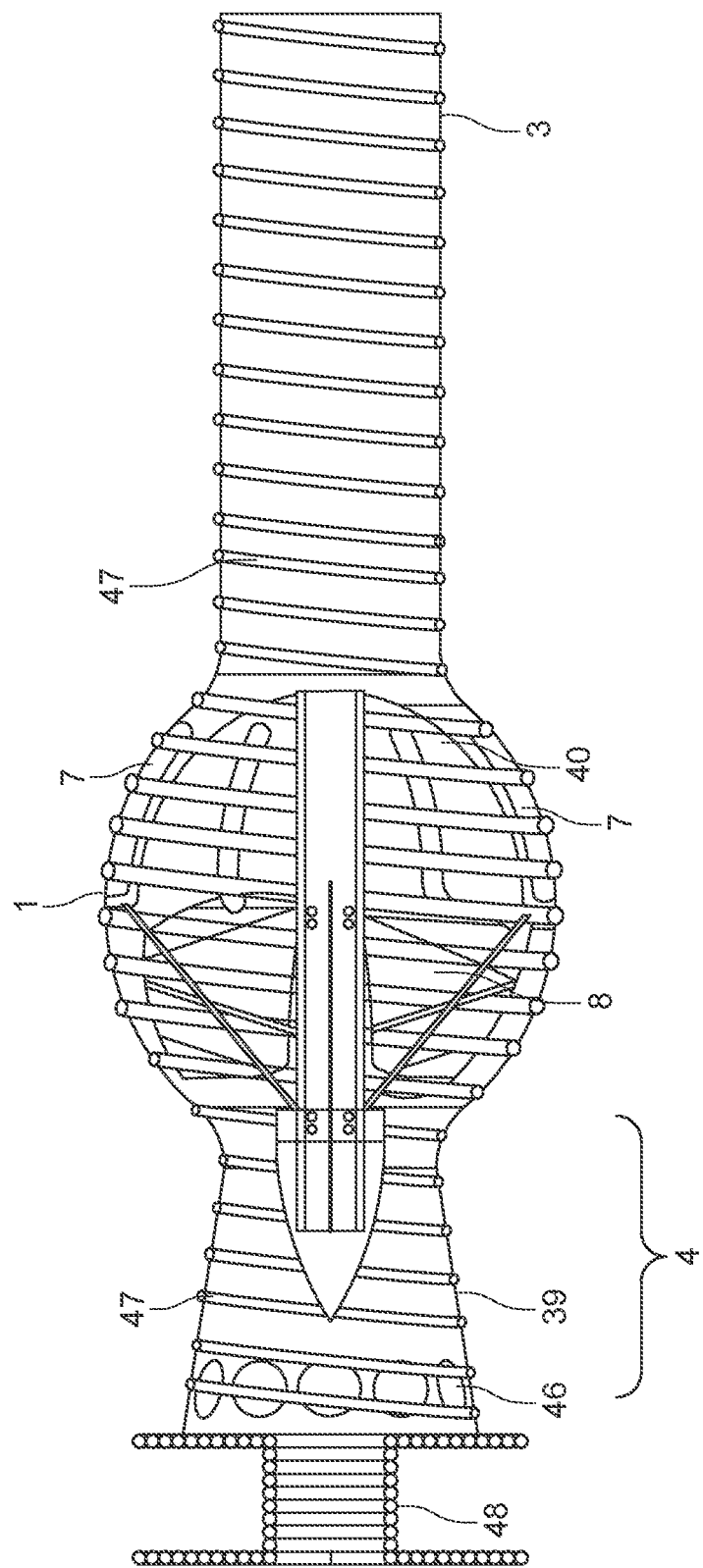

FIG. 11 shows the human heart with the stent pump according to the fourth embodiment as depicted in FIG. 10 in its folded, unexpanded state when being implanted by transseptal delivery in the left atrium, FIG. 12 shows the human heart with the stent pump according to the fourth embodiment as depicted in FIG. 10 in its unfolded, expanded state, FIG. 13 shows a sectional view of the stent pump according to a fifth embodiment of the invention in its unfolded, expanded state and FIG. 14 shows a sectional view of the stent pump according to a sixth embodiment of the invention in its unfolded, expanded state.

Figure 1A:
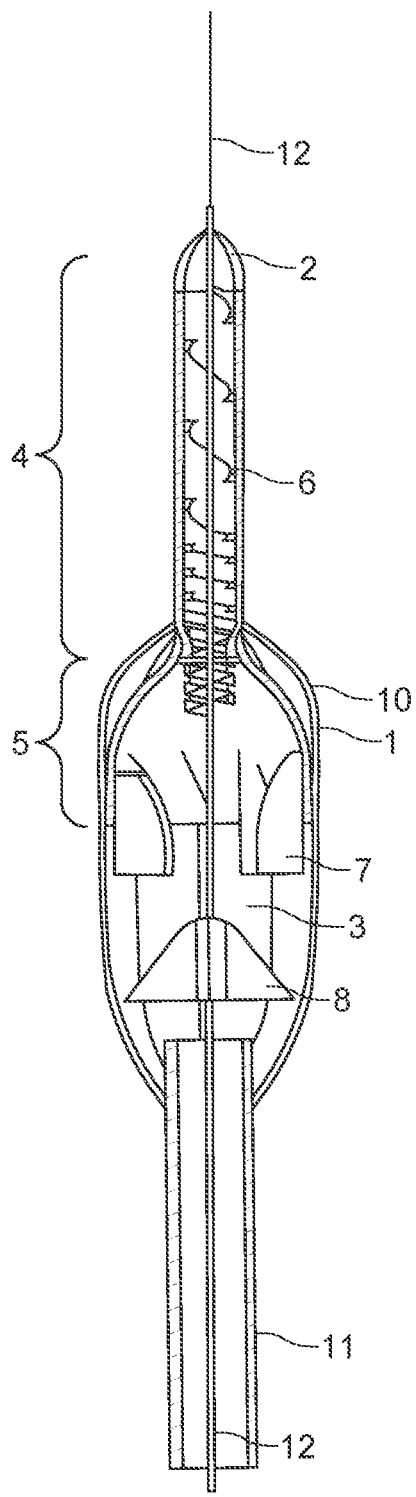
Figure 1B:
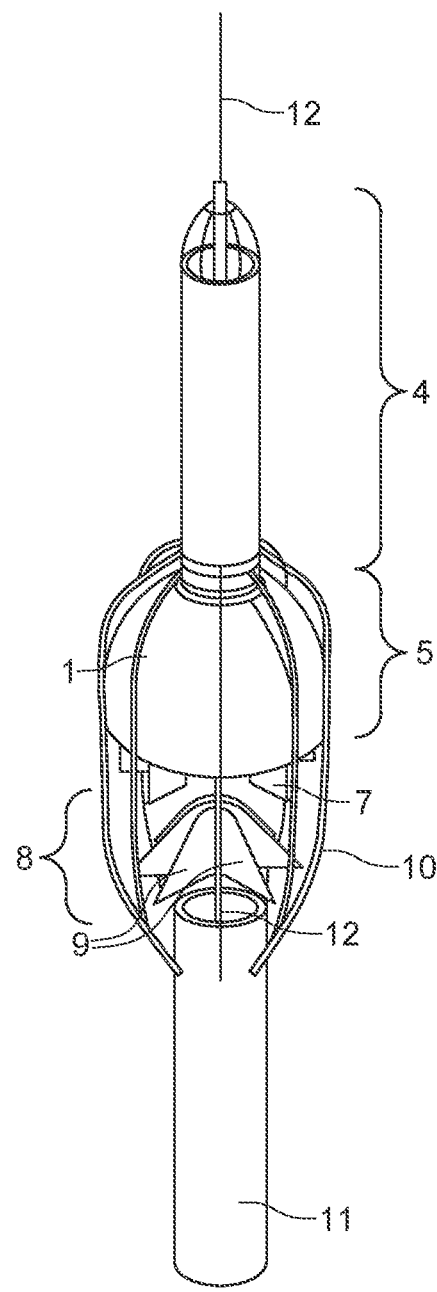

Reference numeral 1 in FIG. 1 depicts the housing 1, which has an inlet 2 arranged on the upstream side of the pump, and an outlet 3 arranged on the downstream side of the pump. In the depicted embodiment the housing 1 is impermeable to blood.

The housing is subdivided in two parts, namely inlet section 4, which serves as a suction hose for conveying the blood, which is being sucked out of the left ventricle, into the housing, and part 5, which shows a wider and conical diameter if compared to part 4.

Inlet section 4 of the housing 1 comprises vanes 6 protruding inwardly from the wall of the housing 1, which impart a rotational flow component to the blood when it enters the housing 1 at inlet 2 and when it subsequently flows through inlet section 4 of the housing 1.

After inlet section 4 the blood reaches part 5 of the housing 1, which is equipped with parallel oriented fins 7, which extend downstream from part 5 of the housing 1 in an axial direction and which act as stream former.

Furthermore, the pump comprises an impeller 8 having a conical body with vanes 9 arranged on its outside.

In the depicted embodiment fixing means 10, which comprise a radially expandable cage, surround the housing 1. On their upstream end the fixing means 10 are fixed to inlet section 4 of the housing 1. In their middle section the fixing means 10 are connected to part 5 of the housing 1. On their downstream end the fixing means 10 are fixed to a tubular piece 11 of the pump.

In the folded state of the pump as depicted in FIG. 1 the impeller 8 and the fins 7 of the stream former are arranged downstream of the housing 1, whereby the impeller 8 is arranged downstream of the fins 7 of the stream former.

Reference numeral 12 depicts a plurality of wires, such as e.g. a guide wire, a rotational wire, which is coupled to the impeller and a drive (not shown), which drives the rotation of the pump, a pushing wire and a stabilizing wire.

FIG. 2 shows the stent pump according to the first embodiment as depicted in FIG. 1 in its unfolded, expanded state.

When being deployed, part 5 of the housing 1 and the impeller 8 expand. The impeller 8 together with the tubular piece 11 are displaced towards the housing 1 so that the impeller 8 gets arranged upstream of the fins 7 of the stream former.

Figure 3:
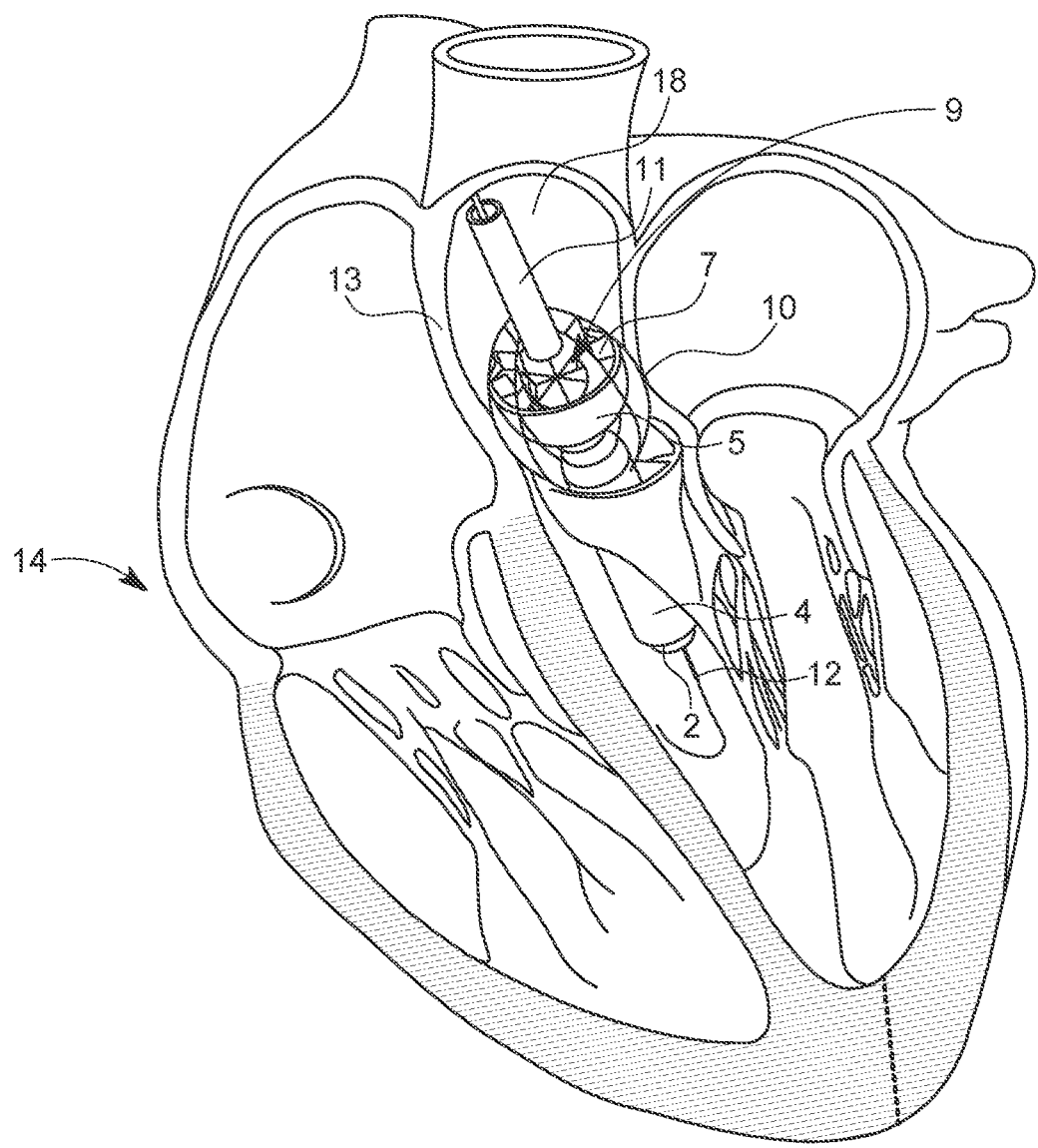
FIG. 3 shows the human heart with the stent pump according to the first embodiment as depicted in FIGS. 1a and 1b and FIGS. 2a and 2b when being implanted in the ascending aorta.

The fixing means 10 also expand in the radial direction when the pump is being deployed until they rest against the vessel wall 13 of the aorta 18 of the human heart 14 (cf. FIG. 3). The fixing means 10 hence function as a stent, which holds the vessel open and fixes the pump in its position.

Due to its rotation the impeller 8 attracts the blood flow according to arrow 15 through the housing 1, where it reaches the vanes 9 of the rotating impeller 8, whereby radial ejection according to arrows 16 against the housing 1 and conveyance of the blood to the fins 7 of the stream former is caused, which subsequently serves for ejecting the blood axially into the vessel according to arrow 17. Hence the bloodstream is redirected (cf. arrows 15, 16 and 17), i.e. the blood flows in an essentially axial direction when leaving the pump, which provides for a laminar flow and the desired damping effect of the blood.

The first embodiment of the device is implanted via intravascular delivery through the aorta 18 of the human heart 14 (cf. FIG. 3).

FIG. 4 shows the stent pump in its folded state according to a second embodiment of the present invention. FIG. 5 shows the stent pump in its unfolded, expanded state according to the second embodiment as depicted in FIG. 4.

The parts, which correspond to the parts as already described with regard to FIGS. 1, 2 and 3, are designated with the same reference numerals.

In the folded state of the pump as depicted in FIG. 4 the impeller 8 and the fins 7 of the stream former are arranged within part 5 of the housing 1, whereby the impeller 8 is arranged downstream of the fins 7 of the stream former.

When being deployed (cf. FIG. 5) part 5 of the housing 1, the impeller 8 and the fins 7 expand and the impeller 8 is pushed further inwards the housing 1, thereby being arranged upstream of the fins 7 of the stream former.

Inlet section 4 of the housing 1 may be perforated, which enables attraction of the blood surrounding the housing to the inside of inlet section 4 of the housing, when the impeller 8—due to its rotation—attracts the blood flow.

The vanes 6 protruding inwardly from the wall of inlet section 4 of the housing 1 impart a rotational flow component to the blood when it enters the inlet 2 and the perforations 29 of inlet section 4 and results in the formation of a funnel-shaped stream towards the pump. The blood flows inside the housing according to arrows 21, where it subsequently reaches the vanes 9 of the rotating impeller 8, which causes radial ejection against the housing 1 according to arrows 22 and conveyance of the blood to the fins 7 of the stream former, which subsequently serves for ejecting the blood axially into the vessel according to arrow 23.

FIG. 6 shows the device according to the second embodiment of FIGS. 4 and 5 when being implanted via apical delivery through the apex 24 into the left ventricle 25 of the human heart 14.

The inlet 2 of the housing 1 is arranged in the left ventricle near the apex 24 of the heart 14. The outlet 3 of the housing 1 opens out into the aorta 18, in the depicted embodiment into the aortic valve 31. The wires 12 are connected to a magnetic coupling 30, which is arranged inside the left ventricle and which wirelessly interacts with a motor 26 arranged outside of the human heart 14. The wireless interaction is depicted by dotted line 32.

FIG. 7 is a perspective view of the impeller 8, which is according to this third embodiment surrounded by a laminated longitudinal helix 29, which completely surrounds the impeller 8 in its axial direction and which extends until it reaches the downstream end (marked with arrow 30) thereof.

FIG. 8 shows a detailed view of the impeller 8, which is built by individual segments, which each comprise a s-shaped vane 9 and a conically formed linker portion 27. Via the linker portions 27 the individual vanes 9 are interconnected, thereby forming the impeller 8.

Furthermore, FIG. 8 shows pulling wires 28, which serve for deployment of the impeller 8 when being pulled.

FIG. 9 depicts a sectional view of the stent pump in its unfolded, expanded state according to the third embodiment of the present invention as shown in FIG. 7. The longitudinal helix 29 is arranged between the inner surface of the housing 1 and the impeller 8 and starts at the inlet 2 of the inlet section 4 of the housing 1 and ends at the upstream region 31 of the fins 7 of the stream former, i.e. continues into the fins of the stream former. According to said third embodiment the longitudinal helix serves as means for imparting a rotational flow component to the blood when entering the stent pump and flowing through the same and hence favors a smooth entry of the blood stream into the impeller region 5 and furthermore also a smooth entry of the blood stream into the stream former region 32.

FIG. 10 shows a sectional view of the stent pump according to a fourth embodiment of the invention in its unfolded, expanded state. Within the housing 1, which has an inlet 2 arranged on the upstream side of the pump, and an outlet 3 arranged on the downstream side of the pump, an impeller 8 is arranged upstream of the fins 7 of a stream former. Further, funnel shaped means 33 are arranged upstream of the impeller 8, which direct the blood from the inlet 2 to the impeller 8 and the fins 7 of the stream former according to arrows A when the impeller 8 is rotated.

Rotation of the impeller 8 is achieved via motor 26, which is arranged transeptally (Septum of the heart is denoted by 34) and which interacts with a drive shaft 39 in a contactless manner, i.e. by means of a magnetic coupling, wherein the drive shaft 39 reaches through the funnel shaped means 33 and is connected to the impeller 8 on its downstream side.

FIG. 11 shows the human heart 14 with the stent pump according to the fourth embodiment as depicted in FIG. 10 in its folded, unexpanded state when being implanted via transseptal delivery. In order to implant the stent pump a catheter sleeve 35 carrying all components of the pump is advanced through the vena cava inferior 36 into the right atrium 37. When the right atrium 37 is reached the septum (not shown) between the right atrium 37 and the left atrium 38 is punctured and crossed, whereby the catheter sleeve 35 and the impeller 8 in its folded state are advanced into the left atrium 38. The drive 26 is arranged in the right atrium 37. The housing and other components of the pump are not depicted in FIG. 11.

FIG. 12 shows the stent pump according to the fourth embodiment as depicted in FIG. 10 in its unfolded, expanded state. After reaching the left atrium 38 the impeller 8 is defolded. The inlet section 2 (not shown in FIGS. 11 and 12) of the pump is arranged near the septum 34 of the heart 14 and the impeller 8 is arranged shortly downstream the inlet section 2. The outlet section 3 is built as a long cannula being arranged downstream of the impeller (the stream former and other components of the pump are not shown in FIG. 12) and mouths in the aortic valve 31. When the impeller 8 is rotated the blood is directed towards the aorta 18 according to arrows B.

FIG. 13 shows a sectional view of the stent pump according to a fifth embodiment of the invention in its unfolded, expanded state. The pump comprises a tapering cross section 39 with perforations 46 at the inlet section 4 of the housing 1. The blood enters the housing 1 via the perforations 46 and is accelerated when being sucked through the tapering cross section 39 of the housing 1 towards the rotating impeller 8. The impeller 8 is arranged upstream of a balloon 40 and fins 7 of a stream former, whereby the impeller 8 and the balloon 40 are rotatably mounted on a mandrel 41, which is coupled to a drive.

Due to its rotation the impeller 8 attracts the blood flow according to arrow 42 through the inlet section 4 of the housing 1, whereupon the blood reaches the vanes 9 of the rotating impeller 8 and is conveyed in a radially outward direction according to arrows 44 and pushed into an annular channel 43 between the balloon 40 and the wall of the housing 1. The fins 7 of the stream former redirect the blood flow in an axial ejection towards the outlet 3 of the pump according to arrow 45.

FIG. 14 shows a sectional view of the stent pump according to a sixth embodiment of the invention in its unfolded, expanded state, which is similar in construction as the embodiment of FIG. 13. To provide overall stabilization of the pump housing, the housing 1 is stabilized by a longitudinal helix 47. To induce and promote rotation of the blood flow in the inlet section 4, the helix 47 provides helix-shaped flow guide means on the inner surface of the housing in the inlet section 4. In contrast, the helix 47 may be covered on its inner side by a layer in the region of the fins 7 of the stream former and the outlet 3 of the housing 1 to solely stabilize the pump without further rotational induction of the blood flow.

In addition fixation means 48, e.g. a spring for fixing the pump to the heart tissue, e.g. to the foramen ovale are shown.

The invention claimed is:

1. A stent pump for intravascular, intraventricular or intraatrial placement inside the human heart comprising:
   a preferably tubular housing having an inlet and an outlet, an impeller, and
   a stream former, wherein the impeller and optionally the stream former are arranged within the housing, wherein the stream former is arranged downstream of the impeller, and the housing, the stream former and/or the impeller are deployable from a first position, in which the housing, the stream former and/or the impeller are folded for being arranged within a delivery device, into a second, expanded position, in which the housing, the stream former and/or the impeller are deployed, characterized in that the housing comprises an inlet section and an impeller section, the inlet section being arranged upstream of the impeller section, whereby the inlet section comprises a tapering cross section at the orifice to the impeller section, which narrows towards the impeller section, and the housing comprises means for imparting a rotational flow component to the blood, namely guiding elements or vanes protruding inwardly from the wall of the housing, which are arranged in the inlet section of the housing, wherein a direction of rotation resulting from the rotational flow component corresponds to a direction of rotation of the impeller.

2. The pump of claim 1, characterized in that the impeller is arranged to be displaceable in an axial direction relative to the housing between a first and a second axial position, wherein in its first axial position the impeller is arranged outside the housing, when the impeller and the housing are folded for being arranged within a delivery device, and in its second axial position the impeller is arranged within the housing, when said housing and said impeller are deployed.

3. The pump of claim 1, characterized in that the housing and/or the stream former and/or the impeller are made of a shape-memory alloy, preferably of nitinol.

4. The pump of claim 1, characterized in that the pump further comprises a preferably flexible drive for driving a mandrel arranged within the housing and fixed to the impeller.

5. The pump of claim 4, characterized in that it further comprises a magnetic coupling, which couples the mandrel to the drive.

6. The pump of claim 4, characterized in that the mandrel is arranged in a semipermeable tube with a hygroscopic inner surface and a hyperosmolar outer surface.

7. The pump of claim 1, characterized in that the housing has a wall that is impermeable to blood.

8. The pump of claim 7, characterized in that the wall of the housing is configured as a flexible hose or as a cage made of wire or cut from a stent tube and carrying a flexible jacket, a cage or a wire helix made from a laminated wire, the lamination being made of PET, silicone or PTFE.

9. The pump of claim 1, characterized in that the housing comprises fixing means for fixing the housing in a vessel.

10. The pump of claim 9, characterized in that the fixing means comprise a radially expandable and blood permeable element or a radially expandable cage, that surrounds the housing.

11. The pump of claim 10, characterized in that the radially expandable element is formed by a distal section of the housing, which in its expanded state preferably widens in the flow direction.

12. The pump of claim 10, characterized in that the impeller and optionally the stream former is arranged in the radially expandable element.

13. The pump of claim 1, characterized in that the impeller comprises a conical body that carries vanes.

14. The pump of claim 13, characterized in that the vanes of the impeller have a hyperboloid shape.

15. The pump of claim 13, characterized in that the vanes of the impeller are made of preferably foldable wires and/or sheets.

16. The pump of claim 1, characterized in that the stream former comprises substantially parallel fins extending in an axial direction.

* * * * *